Aug. 5, 1975 F. W. ANDERSON Plant Pat. 3,757
DWARF PEACH TREE
Filed Sept. 16, 1974
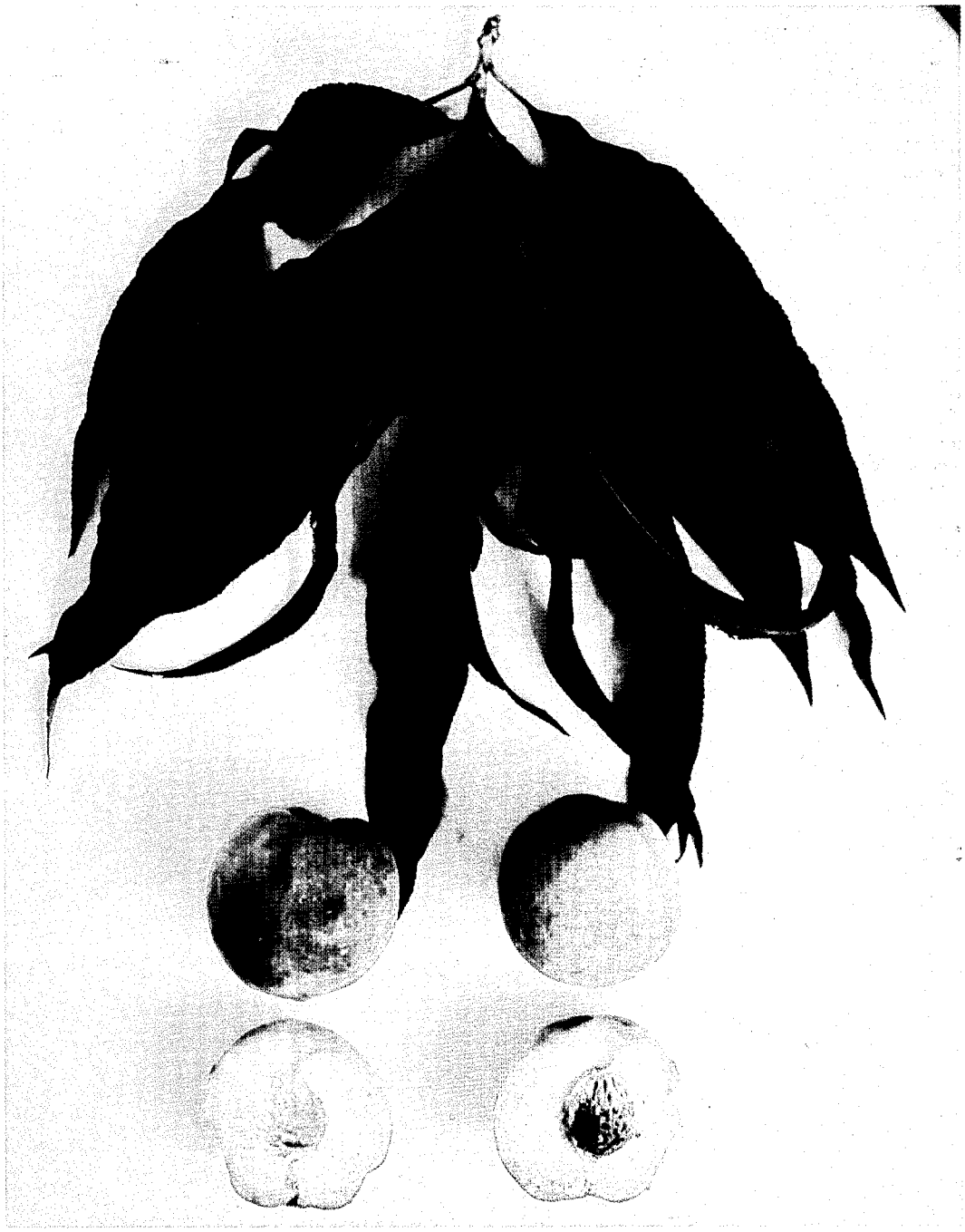

United States Patent

Plant Pat. 3,757
Patented Aug. 5, 1975

3,757
DWARF PEACH TREE

Frederic W. Anderson, Merced, Calif., assignor to
L. E. Cooke Co., Visalia, Calif.

Filed Sept. 16, 1974, Ser. No. 506,752
Int. Cl. A01h *5/03*
U.S. Cl. Plt.—43 1 Claim

ABSTRACT OF THE DISCLOSURE

A genetically dwarf peach tree of medium size, vigorous, spreading, foliated with large lanceolate leaves having a crenate margin, and productive of uniform, medium size, symmetrical, lobose, freestone fruit having yellow skin partially overspread with red, and yellow flesh.

BACKGROUND OF THE VARIETY

Over a substantial number of years I have engaged in an extensive and continuing plant breeding program at my experimental nursery and orchard located near Le Grand, Merced County, California; one purpose of such program being to provide improved varieties of fruit trees. The present variety of dwarf peach tree resulted from my endeavors in the conduct of such plant breeding program.

ORIGIN OF THE VARIETY

The present variety of dwarf peach tree was originated by me in my experimental nursery and orchard, located as aforesaid, as an open-pollinated seedling of the Empress dwarf peach (U.S. Plant Pat. No. 2,533); such seedling having been grown under condition of careful and continuing observation. When such seedling bore fruit, I recognized that it was a new and distinct variety, and I, therefore, selected it for asexual reproduction in anticipation of ultimate commercialization thereof.

ASEXUAL REPRODUCTION OF THE VARIETY

The variety was successfully asexually reproduced by me in my said experimental orchard by top-working on established trees therein, and—in maturity—such reproductions ran true to the parent in all respects.

SUMMARY OF THE VARIETY

The present variety of genetically dwarf peach tree is of medium size, vigorous, spreading, foliated with large lanceolate leaves having a crenate margin, and productive of uniform, medium size, symmetrical, globose, freestone fruit having yellow skin partialy overspread with red, and yellow flesh; the fruit being somewhat similar to that of the Empress dwarf peach tree (the seed parent), but ripens over one month earlier, is somewhat larger, and is of better eating quality.

BRIEF DESCRIPTION OF THE DRAWING

The drawing is an illustration, by photographic reproduction in color, of a twig with leaves, and separate fruit; one of the latter being cut into halves to expose the flesh, and with the stone remaining in one half.

DESCRIPTION OF THE VARIETY

The botanical details of this new and distinct variety of dwarf peach tree—with color definitions (except those in common color terms) referenced to Maerz and Paul Dictionary of Color—are as follows:

Tree:
- *Class.*—Genetically dwarf.
- *Size.*—Medium.
- *Vigor.*—Vigorous.
- *Growth.*—Spreading.
- *Production.*—Productive.

Trunk:
- *Size.*—Medium.

Branches:
- *Size.*—Medium.

Leaves:
- *Size.*—Large. Average length — 9¾". Average width—1 11/16".
- *Form.*—Lanceolate. Acutely pointed.
- *Thickness.*—Medium.
- *Margin.*—Crenate.
- *Petiole.*—Medium length.
- *Glands.*—Average number and position—usually 2 on petiole, and 2 or 3 on blade. Alternate. Medium size. Reniform.
- *Color.*—Top Side—Medium green (23–L–8). Under Side—Lighter Green (22–L–7).

Flower buds:
- *Size.*—Large to medium.

Flowers:
- *Blooming period.*—March 2–March 10, 1974. Medium, as compared with other varieties.
- *Size.*—Large.
- *Color.*—Pink.

Fruit:
- *Maturity when described.*—Eating ripe—June 15, 1974.
- *Date of first picking.*—June 5, 1974.
- *Date of last picking.*—June 15, 1974.
- *Size.*—Uniform. Medium. Average diameter axially—2⅜". Average transversely in suture plane—2 7/16".
- *Form.*—Uniform. Symmetrical. Globose.
- *Suture.*—Shallow. Extends from base to apex, with slight depression beyond pistil point.
- *Cavity.*—Circular. Average depth—½". Average breadth—¾".
- *Base.*—Rounded.
- *Apex.*—Short.

Skin:
- *Thickness.*—Medium.
- *Texture.*—Medium.
- *Tendency to crack.*—None noted.
- *Down.*—Moderate.
- *Color.*—Yellow (9–L–6) partially overspread with red (5–L–4), with some mottling.

Flesh:
- *Texture.*—Medium to soft. Melting.
- *Ripens.*—Evenly.
- *Flavor.*—Mild.
- *Aroma.*—Distinct.
- *Eating quality.*—Fair to good.
- *Color.*—Yellow (10–L–3). Surface of pit cavity—Yellow (10–J–2).

Stone:
- *Type.*—Free.
- *Size.*—Medium. Average length.—1 3/16". Average breadth—1 1/16". Average thickness—9/16".
- *Form.*—Obovoid.
- *Sides.*—Equal.
- *Tendency to Split.*—Slight.
- *Color.*—Beige (11–H–5).

Use: Market—local. Dessert.
Keeping quality: Medium.
Resistance to insects and diseases: No unusual susceptibilities noted.
Shipping quality: Medium to poor.

The dwarf peach tree and its fruit herein described may vary in slight detail due to climatic and soil conditions under which the variety may be grown; the present description being of the variety as grown in the Central Valley of California.

I claim:

1. A new and distinct variety of genetically dwarf peach tree, substantially as illustrated and described, which is of medium size, vigorous, spreading, foliated with large lanceolate leaves having a crenate margin, and productive of uniform, medium size, symmetrical, globose, freestone fruit having yellow skin partially overspread with red, and yellow flesh; the variety being particularly characterized, in comparison with the Empress dwarf peach tree (the seed parent), by fruit which ripens over a month earlier, is somewhat larger, and is of better eating quality.

No references cited.

ROBERT E. BAGWILL, Primary Examiner